United States Patent [19]

Inderbitzen et al.

[11] Patent Number: 5,792,300
[45] Date of Patent: Aug. 11, 1998

[54] PERFUSION CATHETER AND STRIPED EXTRUSION METHOD OF MANUFACTURE

[75] Inventors: Mark Inderbitzen, Miramar; Stephen Querns, Boca Raton, both of Fla.

[73] Assignee: Cordis Corporation, Miami, Fla.

[21] Appl. No.: 685,773

[22] Filed: Jul. 24, 1996

Related U.S. Application Data

[63] Continuation of Ser. No. 184,601, Jan. 21, 1994, abandoned.

[51] Int. Cl.$^6$ .......................... B29C 47/04; B29C 65/00
[52] U.S. Cl. .................. 156/244.13; 156/294; 264/173.16
[58] Field of Search .......................... 156/294, 244.13, 156/244.15; 264/171.26, 173.12, 173.16, 515; 604/96, 97, 98, 282, 101, 102, 103; 606/192, 194

[56] References Cited

U.S. PATENT DOCUMENTS

| | | |
|---|---|---|
| 3,528,869 | 9/1970 | Dereniuk .................. 156/294 |
| 3,889,686 | 6/1975 | Duturbure . |
| 4,183,102 | 1/1980 | Guiset . |
| 4,233,983 | 11/1980 | Rocco . |
| 4,423,725 | 1/1984 | Baran et al. . |
| 4,447,227 | 5/1984 | Kotsanis . |
| 4,581,017 | 4/1986 | Sahota . |
| 4,585,000 | 4/1986 | Hershenson . |
| 4,641,653 | 2/1987 | Rockey . |
| 4,694,827 | 9/1987 | Weiner et al. . |
| 4,723,549 | 2/1988 | Wholey et al. . |
| 4,762,130 | 8/1988 | Fogarty et al. . |
| 4,763,653 | 8/1988 | Rockey . |
| 4,771,777 | 9/1988 | Horzewski et al. . |
| 4,787,388 | 11/1988 | Hofmann . |
| 4,790,315 | 12/1988 | Mueller, Jr. et al. . |
| 4,795,427 | 1/1989 | Helzel . |
| 4,820,271 | 4/1989 | Deutsch . |
| 4,832,028 | 5/1989 | Patel . |
| 4,857,054 | 8/1989 | Helfer . |
| 4,877,031 | 10/1989 | Conway et al. . |
| 4,878,495 | 11/1989 | Grayzel . |
| 4,892,519 | 1/1990 | Sponger et al. . |
| 4,909,252 | 3/1990 | Goldberger . |
| 4,983,167 | 1/1991 | Sahota . |
| 5,000,734 | 3/1991 | Boussignac et al. . |
| 5,000,743 | 3/1991 | Patel . |
| 5,006,119 | 4/1991 | Acker et al. . |
| 5,019,042 | 5/1991 | Sahota .................. 604/101 |
| 5,035,694 | 7/1991 | Kasprzyk et al. . |
| 5,046,503 | 9/1991 | Schneiderman . |
| 5,078,685 | 1/1992 | Colliver . |
| 5,087,247 | 2/1992 | Horn et al. . |
| 5,090,958 | 2/1992 | Sahota . |
| 5,090,960 | 2/1992 | Don Michael . |
| 5,108,370 | 4/1992 | Walinsky . |
| 5,129,883 | 7/1992 | Black . |
| 5,135,474 | 8/1992 | Swan et al. . |
| 5,137,513 | 8/1992 | McInnes et al. . |
| 5,147,377 | 9/1992 | Sahota . |
| 5,152,277 | 10/1992 | Honda et al. . |
| 5,160,321 | 11/1992 | Sahota . |

(List continued on next page.)

FOREIGN PATENT DOCUMENTS

| | | |
|---|---|---|
| 537801 | 3/1957 | Canada . |
| 1392291 | 4/1975 | United Kingdom ............. 264/173 |

*Primary Examiner*—Steven D. Maki
*Attorney, Agent, or Firm*—Lockwood, Alex, Fitz-Gibbon & Cummings

[57] ABSTRACT

A dilation catheter for use in medical procedures is provided including a dilation balloon disposed on the distal end of a flexible tubular shaft. The balloon has perfusion characteristics and may be varied between a collapsed condition and an expanded condition by the introduction of fluid into the balloon. The balloon includes a compliant portion which extends radially outwardly when the balloon is in its expanded condition for engaging a body vessel wall and a non-compliant longitudinal section which traverses the length of the balloon and does not extend radially outwardly when the balloon is in its expanded condition, forming a perfusion channel.

6 Claims, 1 Drawing Sheet

U.S. PATENT DOCUMENTS

| | | |
|---|---|---|
| 5,181,911 | 1/1993 | Shturman . |
| 5,195,955 | 3/1993 | Don Michael . |
| 5,195,971 | 3/1993 | Sirhan . |
| 5,222,941 | 6/1993 | Don Michael . |
| 5,226,888 | 7/1993 | Arney . |
| 5,226,899 | 7/1993 | Lee et al. ................................. 604/282 |
| 5,232,446 | 8/1993 | Arney . |
| 5,261,879 | 11/1993 | Brill . |
| 5,270,086 | 12/1993 | Hamlin ..................................... 606/192 |
| 5,295,959 | 3/1994 | Grubel et al. ............................. 604/96 |
| 5,295,960 | 3/1994 | Aliahmad et al. ........................ 604/103 |
| 5,295,995 | 3/1994 | Kleiman ................................... 606/194 |
| 5,308,356 | 5/1994 | Blackshear, Jr. et al. ............... 606/194 |

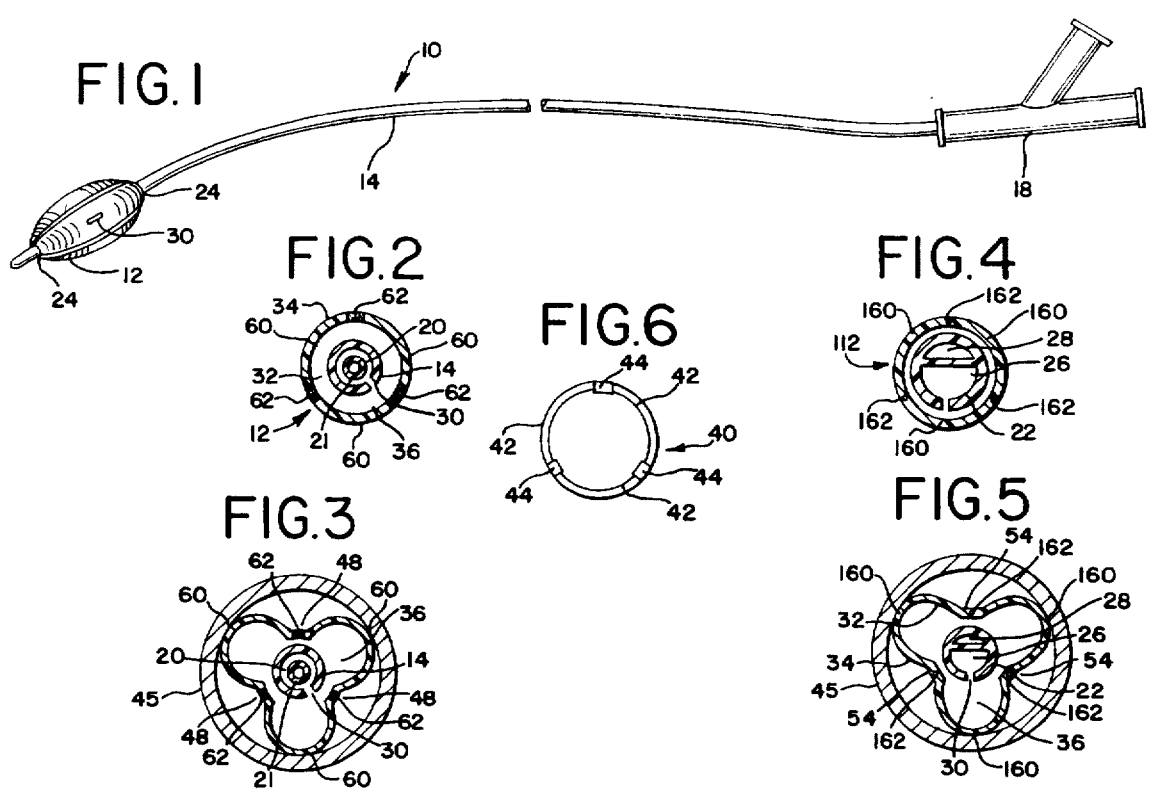

PERFUSION CATHETER AND STRIPED EXTRUSION METHOD OF MANUFACTURE

This application is a continuation of application Ser. No. 184,601, filed Jan. 21, 1994, now abandoned.

The present invention relates generally to dilation catheters suitable for percutaneous transluminal coronary angioplasty procedures (PTCA), and more particularly to dilation catheters for use in PTCA procedures wherein blood is perfused distally of the dilation balloon during the inflation cycle of the balloon as well as a method for manufacturing dilation balloons which themselves have perfusion characteristics.

BACKGROUND AND SUMMARY OF THE INVENTION

PTCA procedures generally include inflation of a balloon in an arterial passageway in an effort to clear a flow path for blood by dilating the stenosis. Inflation of the balloon and subsequent deflation and removal of the balloon results in treatment of the stenosis to increase the available cross-sectional area for blood to flow through the arterial passage.

In typical PTCA procedures, a guiding catheter is inserted into the cardiovascular system through the Tee-brachial or femoral arteries, generally under local anesthesia, until the distal tip of the catheter is in a coronary artery and generally positioned adjacent a stenosis. An extensible balloon of a dilation catheter is advanced through the guiding catheter alone or over a previously introduced guidewire until the balloon is positioned across the stenosis. The balloon is then inflated to a predetermined size with a fluid, preferably a radiopaque liquid, to radially compress the inside of the artery wall, thereby dilating the lumen of the artery. The balloon is then deflated so that the dilation catheter can be removed, and blood flow resumed through the dilated artery that now has a larger cross-sectional area to permit a greater volume of blood to flow therethrough.

In typical PTCA procedures, when the balloon of a dilation catheter is inflated in a coronary artery, all flow ceases through the coronary artery. If blood flow ceases for too long a period of time, the part of the heart which that coronary artery serves can begin to suffer from lack of blood, or ischemia. If the balloon remains inflated in the artery for prolonged periods of time, the injury caused by the absence of blood flow can be irreversible in some cases. On the other hand, it has been found that the probability of an artery wall or the stenosis maintaining its dilated cross-sectional area after having been subjected to dilation from an extensible balloon is directly related to the length of time that the balloon is inflated while located across the stenosis. However, the aforementioned potential problems associated with blocking blood flow are increased the longer the balloon is inflated in the artery.

Attempts have been made to produce dilation catheters that perfuse blood through a catheter or balloon when the balloon is inflated to avoid ischemia conditions distally of the balloon. For example, Wijay, et al., U.S. Pat. No. 5,158,540, disclose a perfusion catheter that perfuses blood during the balloon's inflation cycle to allow for longer inflation periods; however, the catheter is extremely complicated structurally and expensive to manufacture.

It is, therefore a general object of the present invention, to provide a balloon dilation catheter suitable for PTCA procedures and which has perfusion characteristics.

Another object of the invention is to provide a modified dilation catheter and procedure of its use for PTCA procedures wherein blood perfuses around the inflated balloon and permits prolonged inflation times for the balloon.

Another object of the present invention is to provide a perfusion balloon which is formed by extruding two dissimilar polymers, one of which is more elastic than the other.

The present invention overcomes the problems associated with the prior art perfusion catheters by providing a perfusion balloon catheter with a balloon that may be varied between a collapsed condition of a size allowing the catheter to be transported through a body vessel and an expanded condition of a size allowing the exterior surface of the balloon to engage a body vessel wall. The balloon is extruded from an elastic polymer and an inelastic polymer. The portion of the balloon made from the elastic polymer expands radially when the balloon is inflated while the inelastic portion which traverses the length of the balloon does not radially expand. A channel for perfusing fluid past the expanded balloon is thereby formed along the balloon defined by the inelastic portion, the channel being further defined by the expanded elastic portions of the balloon.

For a complete understanding of the present invention, reference is made to the embodiments illustrated in greater detail in the accompanying drawings and described by way of example. It should be understood that this invention is not limited to the particular embodiments illustrated herein, but is defined by the appended claims.

BRIEF DESCRIPTION OF THE DRAWINGS

FIG. 1 is a perspective view of a perfusion balloon catheter made according to the present invention;

FIG. 2 is a cross-sectional view of a portion of the catheter of FIG. 1 illustrating the balloon in its collapsed condition;

FIG. 3 is a cross-sectional view of the catheter of FIG. 2, shown in its expanded condition and disposed within a body vessel, illustrated in cross-section;

FIG. 4 is a cross-sectional view of an alternative embodiment of a catheter made according to the present invention;

FIG. 5 is a cross-sectional view of the catheter of FIG. 4 shown in its expanded condition and disposed within a body vessel, illustrated in cross-section; and FIG. 6 is an end view of an extrusion outlet die of a type suitable for use in making a parison to be molded into a balloon according to the present invention.

DETAILED DESCRIPTION OF THE PREFERRED EMBODIMENT

While the invention may be embodied in a variety of forms and used in different applications such as angioplasty, valvuloplasty, and urological uses, a description of particular embodiments of the inventive concept will be made in the form of dilation catheters for use in PTCA procedures. As illustrated in the drawings, the perfusion balloon catheter, generally designated at 10 in FIG. 1, made according to the present invention comprises an extensible balloon 12 located substantially near the distal end of an elongated flexible tubular shaft 14. The illustrated catheter includes a hub 18, of a type well known in the art. Any suitable fitting and/or hub can be provided as desired.

As shown in FIGS. 2 and 3, a lumen 20 is formed in tubular shaft 14 and may be of a substantially small diameter similar to that of the outer diameter of a standard guidewire, preferably having a diameter of between about 0.008 inch and about 0.020 inch. Lumen 20 is utilized for carrying fluid, such as radiopaque saline solution or other fluid of a type well known in the art. The fluid carried by lumen 20 is communicated to balloon 12 for inflating and deflating balloon 12. It should be understood that the diameter of lumen 20 is large enough to carry sufficient amounts of fluid for inflating balloon 12 sufficiently quickly. In addition, flexible tubular member 14 includes a lumen 21 coaxial with lumen 20 for carrying a guidewire of a type well known in the art.

An alternative embodiment of the flexible tubular shaft 22 is shown in FIGS. 4 and 5 and illustrates a dual lumen catheter, including lumen 26 and lumen 28. As illustrated, lumen 26 is substantially larger in cross-sectional area than lumen 28 and may be utilized to carry fluid to and from balloon 12 similarly to that of lumen 20. Lumen 28 may be utilized to receive a guidewire to provide assistance in placing the dilation catheter at the appropriate position in a body vessel.

Flexible tubing 14 utilized in making the catheter body of the present invention is of a generally known construction. Catheter body is preferably formed of a suitable thermoplastic material, such as polyethylene, polyvinylchloride, and the like, or from a composite structure. Fluid is communicated from the catheter tube to the interior of the balloon through opening 30 shown in FIG. 2. It is preferred that the opening 30 be a slit that extends longitudinally with the flexible tube to prevent propagation of the openings while the tube 14 is being manipulated during insertion into a body vessel. Other shapes of openings and connections, such as circular openings, may also be utilized to pass fluid between the tubing shaft 14 and the interior of the balloon 12. Although one opening is illustrated between the flexible tube 14 and balloon 12, any number of openings may be utilized to pass fluid between the flexible tube and the interior of the balloon 12. Alternatively, a separate lumen may extend from the proximal end of the balloon to pass fluid into and out of the interior compartment of the balloon to inflate and deflate the balloon.

The balloon 12 is generally cylindrically shaped and includes an inner surface 32 and an exterior surface 34. The balloon is in seal providing communication about its respective edges 24 to the flexible tube, defining an interior compartment 36. The balloon is connected to the tubular member by heat sealing, adhesives, or other means for sealing well known in the art. The balloon may be inflated to an expanded condition by the introduction of fluid into interior compartment 36. When fluid is removed from interior compartment 36 the balloon returns to a collapsed condition. A portion 60 of balloon 12 is made from a compliant material and traverses the length of balloon 12. A plurality of such portions 60 may be included. Each portion 60 extends radially away from tubular shaft 14 when fluid is introduced into compartment 36. Another portion 62 of balloon 12 is made from a non-compliant material and traverses the length of balloon 12. Portion 62 remains in a substantially fixed position with respect to tubular shaft 14, and does not radially extend away from tubular shaft 14 to a great extent when fluid is introduced into compartment 36.

Balloon 12 is made from a parison that is extruded from two dissimilar polymers such as through the co-extrusion outlet die 40 illustrated in FIG. 6. The die includes thin arcuate cavity sections 42 for extruding compliant or elastic material and wider and arcuately shorter cavity sections 44 for extruding non-compliant or inelastic material simultaneously to form the balloon. Although die 40 is shown with three thin sections 42 and three wide sections 44, any number of alternating thin and wide sections may be utilized in the die outlet to form the parison of the present invention. Thereafter, the parison typically is subjected to blow molding and the like in order to thin down the walls of the parison, especially those extruded through thin cavity sections 42, and thereby form the balloon.

It is preferred that the compliant or elastic portion 60 be made of a material that exhibits compliance adequate to expand as discussed herein. Examples include polyethylene, latex rubber, polyvinyl chloride, nylon, polyamide, or other suitable flexible, and somewhat elastic material. Preferably, the material will be at least as compliant as nylons such as Nylon 12.

It is preferred that the portion 62 of the balloon extruded from non-compliant material remain in a relatively fixed radial position with respect to the flexible tubular member and be substantially inelastic even when the balloon is inflated. Examples include rigid polyethylene, polyethylene terephthalate, rigid nylon, rigid polyurethane, or other relatively inelastic materials. In some instances, the same material may be used on the inelastic portion and the elastic portion, with the difference in physical characteristics being due to different Durometer values. For example, polyethylene having a relatively low Durometer value characteristic of medical device balloons may be selected for the compliant material while a more rigid polyethylene having a higher or harder Durometer value may be selected for the non-compliant material.

When used, the balloon 12 will be varied between the collapsed condition as illustrated in FIG. 2 and the expanded condition as illustrated in FIG. 3. In its expanded condition, the exterior surface 34 of compliant portion 60 of the balloon extends radially away from the tubular shaft 14 for engaging and dilating the body vessel wall 45 and a stenosis or the like thereon. When the balloon is expanded, the non-compliant portion 62 of balloon 12 does not extend radially away from tubular shaft 14 for any substantial amount. Instead, a longitudinally extending channel 48 is formed that extends across the exterior surface of the balloon and traverses a path that runs substantially the entire length or longitudinal extent of the balloon. Channel 48 is spaced radially inwardly from the extended exterior surface. It will be appreciated that non-compliant portion 62 can move radially outwardly under expansion, but any such movement will be much less than the radial movement of the compliant portions 60 so the longitudinal channel 48 is distinctly defined. When the balloon is expanded in a body vessel, the longitudinal channel 48 permits fluid to flow past the inflated balloon without the need for extrinsic pumping or routing mechanisms.

In a typical procedure according to the present invention, a balloon catheter is generally advanced as desired, such as from the femoral artery or the Tee-brachial artery up the aortic root and positioned in the appropriate coronary artery. Advancement of the catheter through an artery or body vessel is performed when the balloon is in its collapsed, non-inflated condition. The balloon, which is disposed at or near the distal end of the catheter, is positioned across a restriction or stenosis in the artery. Thereafter, the balloon is inflated in the artery by pumping fluid through the lumen of the flexible tubing and into the balloon. Inflation of the balloon extends the balloon radially outwardly causing the compliant portion 60 of exterior surface 34 to engage the stenosis or vessel wall 45 and dilate the vessel wall. Portion 62 of the balloon formed from the non-compliant material does not so extend radially outwardly from the tubular shaft. Channel 48 is spaced radially inwardly from the exterior surface 34 engaging the body vessel wall allowing the blood to be perfused past the expanded balloon. This allows the balloon to remain expanded in the artery for a considerably longer period of time than do conventional catheters as explained above. When deemed necessary, the balloon may then be deflated and rotated and then reinflated to ensure that the entire surface of the stenosis has been effectively dilated.

An alternative embodiment of the perfusion balloon catheter made according to the present invention is illustrated in FIGS. 4 and 5. In this embodiment a dilation balloon catheter including a tubular shaft 22 and balloon 112 are utilized as discussed herein, the main difference being the construction of the balloon. Like reference numerals will therefore be utilized to identify corresponding parts.

As before, the balloon includes portions 160 made from compliant material and portions 162 made from non-complaint material. In this embodiment, however, the non-compliant portions 162 do not extend from the exterior surface 34 to the interior surface 32 of the balloon. The portion 162 made from non-compliant material is imbedded in the balloon, being positioned in the balloon between the exterior surface 34 and interior surface 32 and extending the working length of the balloon. This arrangement allows the exterior surface of the balloon to be extruded as a continuous section of compliant material. One advantage of this arrangement is that the non-compliant material, which is generally of greater hardness than the compliant material, is surrounded by the softer compliant material, decreasing any probability of exerting trauma on the body vessel during insertions of the catheter.

The alternative embodiment of the catheter functions identically to the catheter described before. Thus, when the catheter is disposed in a body vessel 45 as in FIG. 5, the exterior surface of the balloon when the balloon is in its expanded condition, extends radially outwardly from tubular shaft 22 engaging the body vessel wall 45 and dilating the body vessel wall. It should be understood that the portions of the balloon engaging the vessel wall are made from the compliant material. Simultaneously, channels 54 spaced radially inwardly from the exterior surface of the balloon and of the vessel wall are formed and extend longitudinally the length of the balloon, providing a passageway for fluid to be perfused past the expanded balloon. Channels 54 are formed due to portions 162 of the balloon remaining in a substantially fixed position with respect to the tubular shaft 22 and not extending substantially radially outwardly when balloon 112 is in its expanded condition.

It will thus be seen that the present invention provides a new and useful perfusion catheter having a number of advantages and characteristics, including those pointed out herein and others which are inherent in the invention. Preferred embodiments of the invention have been described by way of example, and it is anticipated that modifications may be made to the described forms without departing from the spirit of the invention or the scope of the appended claims.

What is claimed is:

1. A method of forming a perfusion dilation catheter for use in medical procedures comprising the steps of:

providing an extrusion outlet die having a first outlet portion having a first outlet portion opening and a second outlet portion having a second outlet portion opening positioned adjacent said first outlet portion opening;

supplying a first polymer to said first outlet portion;

supplying a second polymer to said second outlet portion, said first polymer being relatively elastic and said second polymer being relatively inelastic;

simultaneously extruding said first polymer through said first outlet portion opening and said second polymer through said second outlet portion opening to provide a co-extrusion for forming a balloon of a dilation catheter for use in medical procedures, said dilation catheter balloon having a distal end and a proximal end, wherein the first polymer of said co-extrusion defines an extensible portion of said dilation catheter balloon and has an exterior surface and the second polymer of said co-extrusion defines a generally non-extensible portion of said dilation catheter balloon, said generally non-extensible portion being positioned in contact with said extensible portion at a location within said exterior surface of said extensible portion and not projecting beyond said exterior surface when said balloon is in a collapsed condition;

connecting said balloon in seal-tight communication to a flexible elongated tubular member at the distal and proximal ends of said balloon such that said dilation catheter balloon is disposed on said tubular member, said balloon being extensible between said collapsed condition of a size allowing said balloon to be transported through a body vessel and an expanded condition of a size allowing a portion of said exterior surface of said extensible portion of said exterior surface of said extensible portion to engage a body vessel wall, said extensible portion of said balloon being a substantially compliant portion and said generally non-extensible portion being a longitudinally extending substantially non-compliant portion, said non-compliant portion defining a longitudinally extending perfusion channel spaced radially inwardly from said compliant portion when said balloon is in its expanded condition; and providing a passageway for passing fluid between said tubular member and said balloon to vary said balloon between its collapsed and expanded conditions.

2. The method of claim 1, wherein said first outlet portion opening of said die extends arcuately.

3. The method of claim 1, wherein said first outlet portion opening is substantially radially narrower than said second outlet portion opening.

4. The method of claim 1, wherein said first outlet portion opening comprises a plurality of circumferentially spaced arcuately extending openings.

5. The method of claim 4, including a plurality of said second outlet portion openings positioned between said plurality of circumferentially spaced arcuately extending first outlet portion openings, and said plurality of second outlet portion openings are circumferentially spaced from each other.

6. The method of claim 1, wherein said first outlet portion opening comprises a continuous annular opening and said second outlet portion includes at least one opening within said annular opening for extruding said second polymer.

* * * * *